United States Patent [19]
Hellmuth et al.

[11] Patent Number: 5,795,295
[45] Date of Patent: Aug. 18, 1998

[54] OCT-ASSISTED SURGICAL MICROSCOPE WITH MULTI-COORDINATE MANIPULATOR

[75] Inventors: Thomas Hellmuth, Aalen; Michael Kaschke, Oberkochen, both of Germany; John C. Moore, Half Moon Bay, Calif.; Gerhard Unold, Essingen, Germany

[73] Assignee: Carl Zeiss, Inc., Thornwood, N.Y.

[21] Appl. No.: 669,948

[22] Filed: Jun. 25, 1996

[51] Int. Cl.⁶ ........................................................ A61B 5/00
[52] U.S. Cl. ................... 600/407; 250/201.3; 359/358; 600/310
[58] Field of Search .................. 128/653.1, 633, 128/664, 665, 920, 922; 351/212, 221; 250/201.3, 330, 358.1, 370.08; 606/130; 359/376, 368; 356/141.1; 382/133; 600/407, 310, 473, 476

[56] References Cited

U.S. PATENT DOCUMENTS

| 5,354,314 | 10/1994 | Hardy et al. | 606/130 |
| 5,491,524 | 2/1996 | Hellmuth et al. | 351/212 |
| 5,506,634 | 4/1996 | Wei et al. | 351/221 |
| 5,622,170 | 4/1997 | Schulz | 128/653.1 |

*Primary Examiner*—Marvin M. Lateef
*Assistant Examiner*—Shawna J. Shaw
*Attorney, Agent, or Firm*—Michael B. Einschlag

[57] ABSTRACT

Embodiments of the present invention provide method and apparatus for use during a neurosurgical procedure to enable a multi-coordinate manipulator ("MCM") to locate blood vessels and nerves in a patient's brain with submillimeter resolution. In addition, embodiments of the present invention provide method and apparatus for mapping oxygenation of brain tissue in three dimensions to differentiate tumor tissue from normal brain tissue with submillimeter resolution.

36 Claims, 2 Drawing Sheets

OCT-ASSISTED SURGICAL MICROSCOPE WITH MULTI-COORDINATE MANIPULATOR

TECHNICAL FIELD OF THE INVENTION

The present invention relates to a surgical microscope which includes an optical coherence tomography ("OCT") apparatus and a multi-coordinate manipulator.

BACKGROUND OF THE INVENTION

The principal risk factors occurring during a neurosurgical procedure are: (a) damage to blood vessels such as arteries; (b) destruction of vital brain tissue; and (c) destruction of, or damage to, nerves. One present technique for avoiding these risk factors entails imaging blood vessels and major nerve bundles using x-ray computer tomography ("CT") and/or nuclear magnetic resonance ("NMR") diagnostic imaging systems. Using diagnostic images provided by such diagnostic imaging systems, a neurosurgeon plans a neurosurgical procedure which attempts to minimize damage to blood vessels, destruction of vital brain tissue and destruction of, or damage to, nerves.

As is well known, a multi-coordinate manipulator ("MCM") is a robot system which is connected to a neurosurgical microscope for use during a neurosurgical procedure. As is well known, diagnostic image data such as CT and/or NMR diagnostic image data ("CT/NMR diagnostic image data") are input to, and stored in, a computer system associated with the MCM (the "MCM-computer-system"). The MCM moves the neurosurgical microscope along (x, y, z) axes and autofocuses the neurosurgical microscope upon locations in the patient's brain that: (a) were specified by an operator such as a neurosurgeon prior to the neurosurgical procedure and were stored in the MCM-computer-system and/or (b) are specified by an operator such as the neurosurgeon during the neurosurgical procedure. As is well known, a display of the stored diagnostic image data is provided on a video display associated with the MCM ("MCM-display").

In a well known technique using the MCM, prior to the neurosurgical procedure, the neurosurgeon views the diagnostic image data on the MCM-display and provides input to the MCM-computer-system by means of an operator/ machine interface ("MCM-operator-interface") such as a light pen. For example, in accordance with this technique, the neurosurgeon indicates several points on the MCM-display and, in response, the MCM-computer-system develops and stores a path connecting the points and displays the path on the MCM-display. Typically, the path corresponds to a boundary separating a brain tumor from normal brain tissue. Then; during the neurosurgical procedure, the MCM-computer-system displays the diagnostic image data and the path on the MCM-display. Next, the MCM moves the neurosurgical microscope and autofocuses it at points along the path in response to operator input. In addition, the operator may provide input through the MCM-operator-interface to cause the MCM to move the neurosurgical microscope and to autofocus it upon chosen locations shown by the MCM-display. As is well known, the MCM can also move a surgical tool such as an electrocautery apparatus and/or a laser apparatus in coordination with the neurosurgical microscope so that the location of effective action of the surgical tool is in the field of autofocus of the neurosurgical microscope. As a result, the neurosurgeon uses the diagnostic image data as a guide to view a portion of the patient's brain and to command the MCM to: (a) autofocus the neurosurgical microscope on an area in the portion of the brain and (b) move a surgical tool to that area for use. Then, if satisfied with the positioning, the neurosurgeon can activate the surgical tool, for example, to cut tissue.

In accordance with well known methods, CT/NMR diagnostic image data are based in a coordinate system whose origin is reproducibly located with respect to an identifiable location on or in the patient's head and whose axes are reproducibly oriented with respect to an identifiable orientation of axes on or in the patient's head. For example, the patient's head is typically placed in an appliance which provides: (a) a reproducible location of an identifiable position of a particular bone structure or an identifiable position of the appliance and (b) an orientation of identifiable axes affixed to the appliance.

In accordance with well known methods, before the neurosurgical procedure begins, the coordinate system of the MCM is set to coincide with the coordinate system of the diagnostic image data by reference to the identifiable position and the identifiable axes referred to above. For this purpose, using the MCM, a neurosurgeon positions the neurosurgical microscope so that a respective reference point of the appliance is visible at the center of the field of view of the microscope. Then, the axial position of the reference point is brought into focus by the autofocus system of the microscope. The MCM coordinates of the respective reference point of the appliance are then stored as a position vector in the MCM-computer-system. This procedure is repeated at least three times because the positions of at least three points (not all on one line) of a three dimensional body are needed to describe the three dimensional position and orientation of that body in space. The coordinate system of the patient and, therefore, the appliance, is identical, within a certain accuracy, to the coordinate system of the CT/NMR diagnostic image data. Within that coordinate system, the coordinates of those reference points are known to the MCM-computer-system as vectors stored in the CT/NMR diagnostic image data set. As is well known to those skilled in the art, a unique linear transformation exists for transforming the position vectors of the reference points in the MCM coordinate system to the respective position vectors of the patient/diagnostic image data coordinate system.

A problem exists in that the location of a brain structure visible through the neurosurgical microscope corresponds to the location of the brain structure provided by the diagnostic image data only with an accuracy on the order of several millimeters. This uncertainty is primarily caused by movement of the brain when the skull is opened at the beginning of the neurosurgical procedure and brain pressure is released. However, an accuracy on the order of several millimeters is not sufficient to avoid damage at positions where blood vessels or nerves are close to or under a path along which the neurosurgeon will remove brain tissue.

In light of the above, there is a need for a method and apparatus for use during a neurosurgical procedure to enable an MCM to locate blood vessels and nerves in a patient's brain with submillimeter resolution.

Additionally, in many neurosurgical procedures, tumor tissue has to be removed. It is important for the success of the neurosurgical procedure that tumor tissue be completely removed without damaging blood vessels, vital brain tissue or nerves. Techniques have been developed to differentiate between tumor tissue and normal brain tissue by attempting to take advantage of metabolic differences between tumor tissue and normal brain tissue. For example, the metabolism of tumor tissue causes the tumor tissue to have a lower oxygen pressure than that of surrounding normal brain tissue. In accordance with one such prior art technique, the oxygenation of brain tissue is measured by measuring a phosphorescence decay lifetime of a phosphorescent probe injected into the systemic blood. This technique is disclosed in an article entitled: "Localization of Tumors and Evaluation of Their State of Oxygenation by Phosphorescence Imaging" by David F. Wilson and George Cerniglia, *Cancer Research*, Vol. 52, Jul. 15, 1992, pp. 3988–3993. The disadvantage of the disclosed optical technique is that only the surface of the tumor tissue is accessible to optical detection and, as a result, the disclosed optical technique provides no information about the tumor tissue below the surface.

In light of the above, there is a need for a method and apparatus for mapping oxygenation of brain tissue in three dimensions to differentiate tumor tissue from normal brain tissue with submillimeter resolution.

SUMMARY OF THE INVENTION

Embodiments of the present invention provide method and apparatus for use during a neurosurgical procedure to enable a multi-coordinate manipulator ("MCM") to locate blood vessels and nerves in a patient's brain with submillimeter resolution. In addition, embodiments of the present invention provide method and apparatus for mapping oxygenation of brain tissue in three dimensions to differentiate tumor tissue from normal brain tissue with submillimeter resolution.

In particular, an embodiment of the present invention is a surgical apparatus for use in performing a surgical procedure on an object which comprises: (a) a surgical microscope; (b) an MCM system which: (i) translates and orients the surgical microscope, (ii) stores diagnostic image data, and (iii) autofocuses the surgical microscope; (c) an optical coherence tomography ("OCT") apparatus which includes: (i) scanning means for scanning the object with optical output from the OCT apparatus in response to input from the MCM system, (ii) for producing OCT scan data in response to reflections of the optical output from the object, and (iii) for transmitting the OCT scan data to the MCM system for analysis.

BRIEF DESCRIPTION OF THE FIGURE

Components which are the same in the various figures have been designated by the same numerals for ease of understanding.

DETAILED DESCRIPTION

Figure 1:
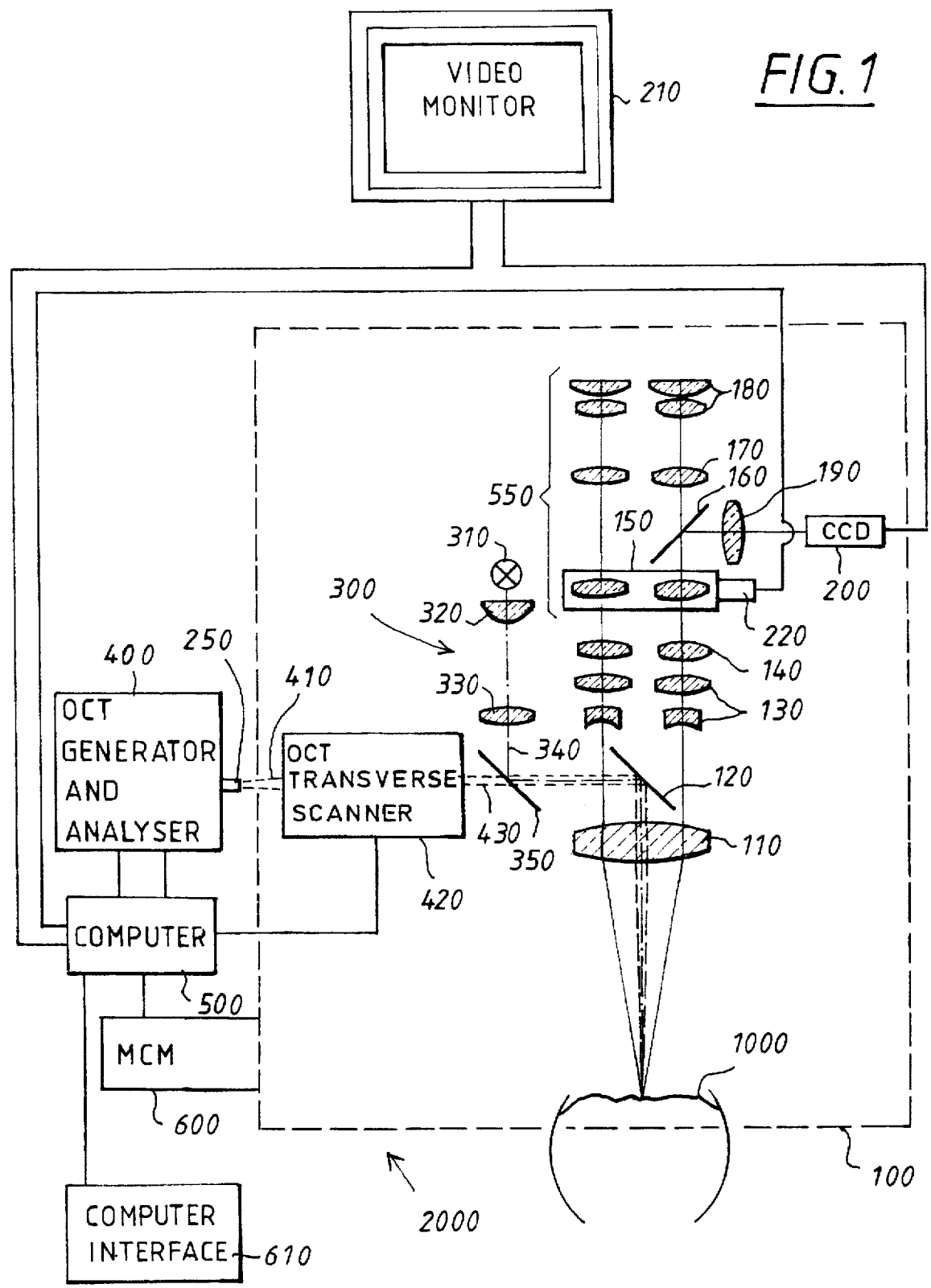
FIG. 1 shows a block diagram of an embodiment of the present invention which comprises a neurosurgical microscope combined with an optical coherence tomography ("OCT") apparatus and a multi-coordinate manipulator ("MCM")

FIG. 1 shows a block diagram of embodiment 2000 of the present invention which comprises neurosurgical microscope 100; multi-coordinate manipulator ("MCM") 600 with associated computer system 500 ("MCM-computer-system 500") and operator/machine interface 610 ("MCM-operator-interface 610"); optical coherence tomography generator and analyzer 400 ("OCT generator and analyzer 400"); optical coherence tomography transverse scanner 420 ("OCT transverse scanner 420"); and video monitor 210.

As shown in FIG. 1, neurosurgical microscope 100 includes objective lens 110 which has a long working distance (~200 mm) for focusing on portions of a patient's brain 1000 during a neurosurgical procedure. Beamcombiner 120 (although shown in FIG. 1 as a beamsplitter, it should be clear to those of ordinary skill in the art that beamcombiner 120 may be embodied in a number of other ways such as, for example, a prism) directs illumination radiation 340 (output from illumination path 300) and OCT beam 430 (output from OCT transverse scanner 420) toward objective lens 110. As shown in FIG. 1, neurosurgical microscope 100 further includes optical magnification changer 130 which is set to provide a magnification suitable for performing a particular neurosurgical procedure. As is well known, optical magnification changer 130 typically includes a number of groups of lenses arranged on a drum for providing varying magnifications such as, for example, 5X, 12X, 20X, and so forth. The radiation impinging upon optical magnification changer 130 is predominantly illumination radiation which has been reflected from a portion of brain 1000 and it is substantially collimated.

Neurosurgical microscope 100 further includes: (a) relay lenses 140 and internal focusing lenses 150. Relay lenses 140 take collimated radiation output from optical magnification changer 130 and form an intermediate image of a portion of brain 1000 and internal focusing lenses 150 take the intermediate image of the portion of brain 1000 formed by relay lenses 140 and provide a collimated beam. Autofocus signals sent to autofocus motor 220 from MCM-computer-system 500 move internal focusing lenses 150 up and down along viewing path 550 to provide a mechanism for internal focus adjustment. Although the embodiment of neurosurgical microscope 100 shown in FIG. 1 indicates that autofocusing is provided by autofocus motor 220 and internal focusing lenses 150, this is merely done for ease of understanding the present invention. In practice, one would utilize autofocusing apparatus such as that shown in U.S. Pat. No. 5,288,987, which patent is incorporated herein by reference. In accordance with the autofocusing apparatus disclosed in U.S. Pat. No. 5,288,987, an autofocus motor can move lenses such as internal focusing lenses 150 or objective lens 110. Further, autofocusing apparatus used to fabricate embodiments of the present invention provide the distance of objective lens 110 from the tissue such as brain tissue 1000 to MCM-computer-system 500.

After passing through internal focusing lenses 150, radiation is collimated and beamsplitter 160 couples a portion of the collimated radiation to video lens 190. The output from video lens 190 impinges upon CCD camera 200 and a video image is provided on at least a portion of the screen of video monitor 210. As those of ordinary skill in the art can readily appreciate, although the use of a single CCD camera is shown, it is within the spirit of the present invention that embodiments may be fabricated utilizing two beamsplitters, i.e., beamsplitter 160 and a similarly placed beamsplitter, to provide stereoscopic viewing through two CCD cameras.

Lastly, tube lenses 170 focus collimated radiation passed through beamsplitters 160 at object planes of eye pieces 180. Eye pieces 180 then provide collimated output which is focused by a viewer's eyes. Since the above-described viewing path 550 is binocular, stereoscopic viewing can be obtained.

As shown in FIG. 1, illumination path 300 includes: (a) incandescent light source 310; (b) condenser lens 320 for collecting radiation output from light source 310; and (c) image lens 330 for filling the entrance pupil of objective lens 110 with the filament of incandescent light source 310. Beamcombiner 350 combines OCT beam 430 (output from OCT transverse scanner 420) with illumination radiation 340 (output from illumination path 300). In a preferred embodiment, beamcombiner 350 is a cold mirror beamsplitter, i.e., a mirror which reflects radiation at lower wavelengths, for example, wavelengths less than about 700 nm, and transmits radiation at higher wavelengths, for example, wavelengths higher than about 700 nm.

Figure 2:
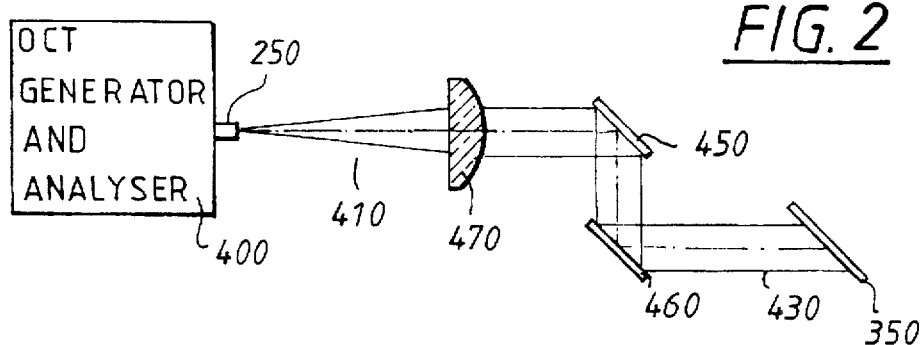
FIG. 2 shows, in pictorial form, an OCT transverse scanner for use in the embodiment of FIG. 1.
Figure 3:
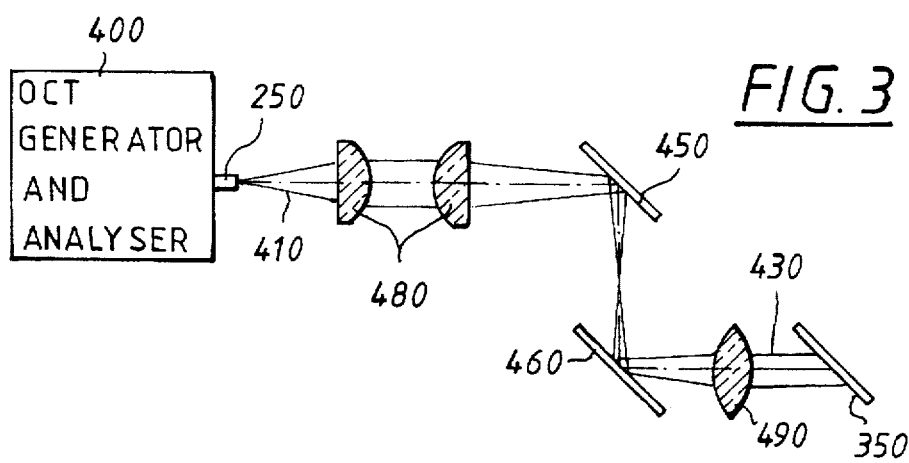
FIG. 3 shows, in pictorial form, another OCT transverse scanner for use in the embodiment of FIG. 1.
Figure 4:
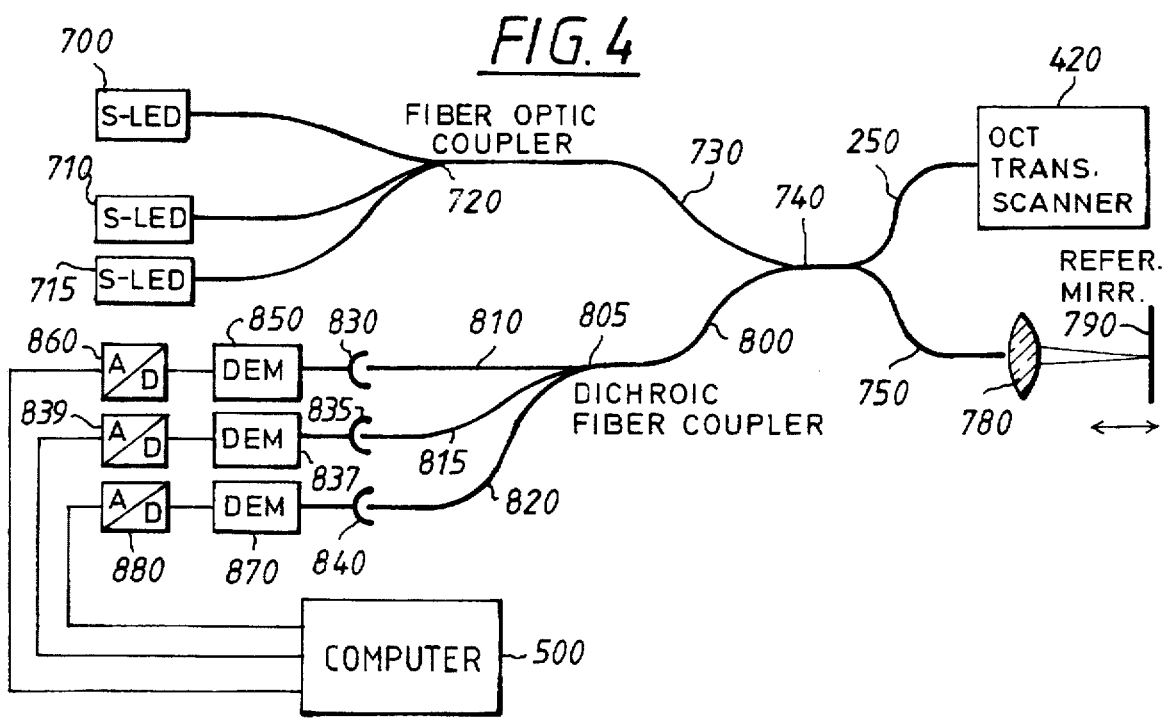
FIG. 4 shows, in pictorial form, a fiber optic embodiment of an OCT generator and analyzer for use in the embodiment of FIG. 1.

FIGS. 2 and 3 show, in pictorial form, first and second embodiments of OCT transverse scanner 420. As shown in FIG. 2, lens 470 collimates OCT radiation 410 output as a point source from fiber 250 of OCT generator and analyzer 400 (an embodiment of OCT generator and analyzer 400 is shown in FIG. 4 and is described in detail below). Further, lens 470 directs the collimated radiation toward scanning mirrors 450 and 460. Scanning mirrors 450 and 460 are orthogonally mounted, galvanometer driven, scanning mirrors which are mounted on a pair of scanning motors (not shown). The scanning motors are operated under the control of MCM-computer-system 500. The manner in which scanning motors 450 and 460 are controlled by, for example, a computer system is well known to those of ordinary skill in the art. In the embodiment shown in FIG. 2, scanning mirrors 450 and 460 are located close to the back focus of objective lens 110 of FIG. 1. Since the back focus of objective lens 110 is close to scanning mirrors 450 and 460, the chief rays of OCT beam 430 are parallel to the optical axis in object space, i.e., the region between objective lens 110 and brain 1000.

As shown in FIG. 3, relay lens 480 transfers OCT radiation 410 output as a point source from fiber 250 of OCT generator and analyzer 400 (an embodiment of OCT generator and analyzer 400 is shown in FIG. 4 and is described in detail below) to an intermediate image. As shown in FIG. 3, the intermediate image is located between scanning mirrors 450 and 460 and scanning mirrors 450 and 460 are located very close to the back focus of scanning lens 490. The chief rays of the OCT beam between scanning mirrors 450 and 460 and brain 1000 in this embodiment are parallel in relay space, i.e., the space between scanning lens 490 and objective lens 110 and the chief rays are focused close to optical axis of objective lens 110. Scanning mirrors 450 and 460 are orthogonally mounted, galvanometer driven, scanning mirrors which are mounted on a pair of scanning motors (not shown). The scanning motors are operated under the control of MCM-computer-system 500. The manner in which scanning motors 450 and 460 are controlled by, for example, a computer system is well known to those of ordinary skill in the art.

FIG. 4 shows, in pictorial form, a fiber optic embodiment of OCT generator and analyzer 400. As shown in FIG. 4, OCT generator and analyzer 400 includes three CW radiation sources 700, 710 and 715, each being, for example, a superluminescent light emitting diode. Light emitting diode 700 preferably operates at wavelengths above 800 nm (preferably at wavelengths substantially around 830 nm), light emitting diode 710 preferably operates at wavelengths below 800 nm (preferably at wavelengths substantially around 750 nm), and light emitting diode 715 preferably operates at wavelengths substantially around 800 nm. Radiation from light emitting diodes 700, 710 and 715 is combined by fiber optic coupler 720 and the combined radiation propagates through fiber 730. The combined radiation propagating in optical fiber 730 is separated into two beams by coupler 740 (for example, a fiber optic coupler) so that output from coupler 740 is coupled into single mode fiber 250 and fiber 750, respectively. Output from fiber 750 is imaged by lens 780 onto reference reflector 790 and output from fiber 250 is directed to OCT transverse scanner 420. As is well known in the art, reference reflector 790 may be embodied in a number of ways, including, without limitation, a substantially planar reflector, a corner cube, and so forth.

As was discussed above with respect to FIG. 1, the output from OCT transverse scanner 420 is directed by beamcombiner 120 and objective lens 110 to impinge upon brain 1000. Then, at least a portion of such radiation is reflected from brain 1000 and coupled back into fiber 250. Next, the radiation reflected from brain 1000 is superimposed by coupler 740 with radiation which is reflected from reference reflector 790 and coupled back into fiber 750. Next, the superimposed radiation output from coupler 740 is coupled into fiber 800. Next, the radiation coupled into fiber 800 is separated by dichroic beamsplitter 805 (for example, a dichroic fiber coupler) into fibers 810, 815 and 820. Radiation having wavelengths substantially around 830 nm is coupled into fiber 810, radiation having wavelengths substantially around 750 nm is coupled into fiber 820, and radiation having wavelengths substantially around 800 nm is coupled into fiber 815. Next, radiation in fiber 810 is detected by detector 830, radiation in fiber 815 is detected by detector 835 and radiation in fiber 820 is detected by detector 840. Next, three separate electronic circuits process the detector signals to generate OCT scan data corresponding to each wavelength region. As is known, for each of the wavelengths, there is an interference between radiation reflected from brain 1000 and radiation reflected from reference reflector 790 if the optical path difference is smaller than the coherence length of the corresponding radiation source. Reference reflector 790 is moved with a substantially constant velocity by means which are well known to those of ordinary skill in the art (not shown) and the position of reference reflector 790 is determined by MCM-computer-system 500 in a manner which is well known to those of ordinary skill in the art. As a result, an interference is detected as a periodic variation of a detector signal output by each of photodetectors 830, 835 and 840, respectively. The periodic variation of each detector signal has a frequency equal to a Doppler shift frequency which is introduced by moving reference reflector 790 with the substantially constant velocity. Output from photodetector 830 is demodulated by demodulator 850; the demodulated output from demodulator 850 is converted to a digital signal by analog-to-digital converter 860 (A/D 860); and the output from A/D 860 is applied as input to MCM-computer-system 500 for analysis. Output from photodetector 835 is demodulated by demodulator 837; the demodulated output from demodulator 837 is converted to a digital signal by analog-to-digital converter 839 (A/D 839); and the output from A/D 839 is applied as input to MCM-computer-system 500 for analysis. Similarly, output from photodetector 840 is demodulated by demodulator 870; the demodulated output from demodulator 870 is converted to a digital signal by analog-to-digital converter 880 (A/D 880); and the output from A/D 880 is applied as input to MCMcomputer-system 500 for analysis. The interference signal vanishes as soon as the optical path difference between radiation reflected from brain 1000 and radiation reflected from reference reflector 790 becomes larger than the coherence length of the respective source. As will be described in detail below, in accordance with one embodiment of the present invention, the images produced by the three radiation sources are used to distinguish between normal brain tissue and tumor tissue. Those of ordinary skill in the art will readily appreciate that an embodiment of the present invention can be fabricated which utilizes only one of light emitting diodes 700, 710 and 715. Such an embodiment would be fabricated, for example, by eliminating light emitting diodes 710 and 715, fiber optic coupler 720, dichroic fiber coupler 805, detectors 835 and 840, demodulators 837 and 870 and A/Ds 839 and 880. Further, those of ordinary skill in the art appreciate that many variations may be made in the embodiment shown in FIG. 4 to accomplish the described finction. For example, and without limitation, equivalent embodiments for the couplers, the fibers, the demodulators, the A/D converters and so forth described above are well known.

MCM 600 of FIG. 1 is interconnected with neurosurgical microscope 100 in a manner which is well known in the art and MCM 600 drives neurosurgical microscope 100 under the direction of MCM-computer-system 500 in a manner which is also well known in the art. However, MCM-computer-system 500 is improved over a conventional MCM-computer-system in accordance with the present invention: (a) to interact with OCT generator and analyzer 400 and OCT transverse scanner 420 and (b) to utilize OCT scan data to enhance the interaction and coordination between MCM 600 and neurosurgical microscope 100. Before providing a detailed description of the improvements, the following provides a description of the conventional aspects of the interaction between MCM 600 and neurosurgical microscope 100 to serve as background and as a basis for more easily understanding the present invention.

As is well known, MCM 600 is a robot system which operates in response to commands received from MCM-computer-system 500. In a typical embodiment, MCM 600 has three motors which drive the three principal axes of MCM 600 in response to signals from MCM-computer-system 500. Driving these three principal axes, MCM 600 can position neurosurgical microscope 100 in three dimensions, for example, along (x, y, z) axes. In addition, neurosurgical microscope 100 is mounted so that three axes of the microscope are driven by three independent motors in response to input from MCM-computer-system 500. By entering commands into MCM-computer-system 500 through MCM-operator-interface 610, an operator can change the position and orientation of neurosurgical microscope 100. In a typical embodiment, the three rotational axes of neurosurgical microscope 100 are located so that the center of rotation of neurosurgical microscope 100 is the center of the focal plane of the microscope.

As is well known, MCM-computer-system 500 sends signals to MCM 600 and to autofocus motor 220. In response to such signals: (a) MCM 600 moves, orients and autofocuses neurosurgical microscope 100 so it focuses upon a selected portion of brain 1000 along a particular direction. In accordance with well known techniques, the selected portion of brain 100 and the orientation: (a) may be specified by an operator such as a neurosurgeon prior to a neurosurgical procedure wherein the coordinates of the selected portion of brain 1000 and the orientation for the view is stored in MCM-computer-system 500 and/or (b) may be specified by the operator during the neurosurgical procedure. As is well known, the neurosurgeon may input information into MCM-computer-system 500 to direct MCM 600 to move and orient neurosurgical microscope 100, to focus on a desired location by using MCM-operator-interface 610 to input such information. For example, in a preferred embodiment, MCM-operator-interface 610 is a light pen which is used to indicate locations on image data displayed on the screen, for example, of video monitor 210. In addition, as is well known, the neurosurgeon may specify a line or a boundary by highlighting several points with the light pen. In response, MCM-computer-system 500 generates a line which passes through the highlighted points and MCM-computer-system 500 transmits data to video monitor 210 which is displayed as the line on the screen of video monitor 210.

As is well known, diagnostic image data, for example x ray computer tomography ("CT") and/or nuclear magnetic resonance ("NMR") generated diagnostic image data, are stored in MCM-computer-system 500. MCM-computer-system 500 transmits such diagnostic image data to video monitor 210 for display on at least a portion of the screen of video monitor 210. For example, video monitor 210 may display an optical image of a portion of brain 1000 seen through neurosurgical microscope 100 and a diagnostic image of the portion of brain 1000 at the same time on the screen of video monitor 210 (side-by-side or overlayed upon each other). In addition, in accordance with well known techniques, MCM-computer-system 500 may transmit stored paths and/or boundaries to video monitor 210 for display, for example, as an overlay of the diagnostic image data displayed on the screen of video monitor 210.

As is well known, the diagnostic image data are based in a coordinate system whose origin is reproducibly located with respect to an identifiable location on or in patient's brain 1000 and whose axes are reproducibly oriented with respect to an identifiable orientation of axes on or in the patient's brain 1000. For example, a patient's head is typically placed in an appliance which provides: (a) a reproducible location of an identifiable position of a particular bone structure or of an identifiable position of the appliance and (b) an orientation of identifiable axes affixed to the appliance.

In accordance with well known methods, before a neurosurgical procedure begins, the coordinate system of MCM 600 is made to coincide with the coordinate system of the diagnostic image data by reference to the identifiable position and the identifiable axes referred to above. For this purpose, using MCM 600, a neurosurgeon positions neurosurgical microscope 100 so that the respective reference point of the appliance is visible at the center of the field of view of microscope 100. The axial position is brought into focus by the autofocus system of microscope 100. In response to commands input through MCM-operator-interface 610, the MCM coordinates of the respective reference point of the appliance are stored as a position vector in MCM-computer-system 500. This procedure is repeated at least three times because the positions of at least three points (not all on one line) of a three dimensional body are needed to describe the three dimensional position and orientation of that body in space. The coordinate system of the patient and, therefore, the appliance, is identical, within a certain accuracy, to the coordinate system of the CT/NMR diagnostic image data. Within that coordinate system, the coordinates of those reference points are known to MCM-computer-system 500 as vectors stored in the CT/NMR diagnostic image data set. As is well known to those skilled in the art, a linear transformation exists for transforming the position vectors of the reference points in the MCM coordinate system to the respective position vectors of the patient/diagnostic image data coordinate system.

Next follows a description of the manner in which MCM-computer-system 500 controls OCT generator and analyzer 400 and OCT transverse scanner 420 to provide OCT scan data in accordance with the present invention. It should be clear to those of ordinary skill in the art that it is not necessary for OCT generator and analyzer 400 and/or OCT transverse scanner 420 to be controlled by MCM-computer-system 500. In particular, it is within the scope of the present invention that they may be controlled by a separate apparatus such as a processor that transmits information to, and receives commands from, MCM-computer-system 500. However, it is preferred to utilize MCM-computer-system 500 to accomplish the described control. Of course, it should also be clear to those of ordinary skill in the art that MCM-computer-system 500 itself may be comprised of one or more processors.

As shown in FIG. 1, OCT generator and analyzer 400 outputs OCT beam 410 from optical fiber 250 under control of MCM-computer-system 500. An embodiment of OCT generator and analyzer 400 is shown FIG. 4 and was described in detail above. As described above, OCT beam 410 output from optical fiber 250 is scanned in a transverse direction by OCT transverse scanner 420 under control of MCM-computer-system 500. Embodiments of OCT transverse scanner 420 are shown in FIGS. 2 and 3 and were described in detail above. The transverse direction lies in a plane (referred to as the transverse plane) that is perpendicular to the axial direction of neurosurgical microscope 100 (the axial direction of neurosurgical microscope 100 lies parallel to the optical axis of objective lens 110). Since, as shown in FIG. 1, OCT transverse scanner 420 is internally coupled to neurosurgical microscope 100, (x, y) coordinates in the transverse plane are known with respect to neurosurgical microscope 100.

As shown in FIG. 4, OCT generator and analyzer 400 comprises reference reflector 790 which is moved at a substantially constant velocity to provide signals which result from radiation reflected from tissue at various depths in brain 1000, the depths correspond to various values along a direction parallel to the axial direction of neurosurgical microscope 100 (referred to as the z axis). In particular, as reference reflector 790 is moved over a distance of the order of several millimeters, reflected OCT scan radiation is received from tissue depths which span a distance (along the z axis) which corresponds to the focusing image of internal focusing lens 150 in the object space of neurosurgical microscope 100. The zero position of reference reflector 790 is chosen so that the resulting z coordinate corresponds to a nominal or predetermined distance of the object plane from objective lens 110.

Thus, as was described above, MCM-computer-system 500 controls and records the (x, y) coordinates of OCT beam 430 in the transverse plane by controlling OCT transverse scanner 420 in a manner that will be described in detail below and MCM-computer-system 500 controls and records the depths from which the OCT scan radiation is reflected from tissue, i.e., their z coordinates, by controlling and recording the position of reference reflector 790. As a result, MCM-computer-system 500 controls and records the (x, y, z) coordinates of OCT beam 430 relative to the (x, y, z) coordinates used to autofocus neurosurgical microscope 100.

In one embodiment of the present invention, scanning mirrors 450 and 460 shown in FIGS. 2 and 3 are each driven with a sawtooth voltage function in a manner which is well known to those of ordinary skill in the art. When the phase and frequency of the respective driver voltages are equal, the resulting scan pattern in the transverse plane is a straight line. When such a linear scan produced by scanning mirrors 450 and 460 is combined with the longitudinal scan into brain 1000 produced by movement of reference reflector 790, an OCT scan in occurs in a plane referred to as the longitudinal OCT scan plane. As one can readily appreciate, the z-axis lies in the longitudinal OCT scan plane. In other words, scanning mirrors 450 and 460 produce a linear, transverse OCT scan and, at predetermined points in the linear, transverse OCT scan, OCT radiation reflected from all scatterers in the path of the OCT radiation, along the z-axis, is compared with radiation from a reference path whose optical length is varied periodically and which optical length is accurately known. As was described above, an OCT output signal is generated only when the optical length of OCT radiation reflected from tissue in brain 1000 is equal to the optical length of the reference path, to within the OCT radiation temporal coherence length. In accordance with the present information, amplitude information is obtained for reflected OCT radiation, as a function of depth along the z-axis into brain 1000, at each of the predetermined points in the linear, transverse scan. Thus, after the OCT scan, MCM-computer-system 500 has collected data which comprises amplitude information over the longitudinal scan plane.

In accordance with the present invention, OCT scan data for a volume of brain 1000 is obtained by rotating the direction of the linear, transverse OCT scan by a predetermined amount by, for example, varying the amplitude of each sawtooth voltage function applied to drive scanning mirrors 450 and 460, in a manner which is well known to those of ordinary skill in the art, to change the orientation of the linear scan and, hence, the orientation of the longitudinal OCT scan plane. The orientation of the linear scan and, hence, the orientation of the longitudinal OCT scan plane is determined by the ratio of the amplitudes of each sawtooth voltage function. Thus, in accordance with the present invention, the longitudinal OCT scan plane can be rotated (the z-axis is the axis of rotation) by varying the ratio of the amplitudes of each sawtooth voltage function. In accordance with this embodiment of the present invention, the longitudinal OCT scan plane is rotated to provide OCT scan data in various longitudinal planes about the z-axis and the data received from the various longitudinal OCT scans is combined by MCM-computer-system 500 to provide three dimensional ("3D") OCT scan data in a volume covered by the multiplicity of longitudinal OCT scan planes. In other words, the direction of the linear, transverse OCT scan is rotated by a predetermined amount in the manner described above, data are collected for the plane at the rotated position, the plane is rotated again, and so forth, until data are collected for the volume. Using such 3D data, MCM-computer-system 500 can provide OCT scan data corresponding to planes having various orientations, not only transverse or longitudinal planes, in the 3D volume and images corresponding to such planes can be displayed on video monitor 210.

In another embodiment of the present invention, the phase of the sawtooth voltage functions described above can be individually adjusted in a manner which is well known to those of ordinary skill in the art to provide a scan in the transverse plane which covers an area. This is referred to as an OCT raster scan. In this embodiment, MCM-computer-system 500 controls reference reflector 790 to cause the OCT radiation to perform a longitudinal scan at various of the (x, y) coordinates of the OCT raster scan in the transverse plane. This provides OCT scan data for slices through brain 1000 (various transverse planes) taken at various values of z, i.e., at various depths. As those of ordinary skill in the art can readily appreciate, the deepest slice will be taken at a depth which provides sufficient transmission of the OCT radiation to provide a detectable signal. During the OCT raster scan, OCT generator and analyzer 400: (a) detects reflected OCT radiation and produces a detection signal; (b) analyzes the detection signal to produce OCT scan data; and (c) transmits the OCT scan data to MCM-computer-system 500. MCM-computer-system 500 analyzes the OCT scan data at predetermined positions of reference reflector 790. The predetermined positions of reference reflector 790 are used to determine the distances of the various transverse planes from objective lens 110, i.e., the z coordinate of the various transverse planes. Thus, as one of ordinary skill in the art can readily appreciate from this, OCT scan data output from OCT generator and analyzer 400 is analyzed by MCM-computer-system 500 to provide images of a number of cross sections of brain tissue at various depths in brain 1000 with a resolution provided by the OCT apparatus, i.e., a resolution in a range of ten to twenty microns. Further, the data received from the various OCT raster scans is combined by MCM-computer-system 500 to provide 3D OCT scan data in a volume covered by the multiplicity of OCT raster scan planes. As was described above, using such 3D data, MCM-computer-system 500 can provide OCT scan data corresponding to planes having various orientations in the 3D volume and images corresponding to such planes can be displayed on video monitor 210.

In accordance with the present invention and as will be described in detail below, the OCT scan data is used in several different inventive methods.

In a first method of utilizing the OCT scan data in accordance with the present invention, MCM-computer-system 500 transmits one or more images of OCT scan data to video monitor 210 for display on at least a portion of the screen of video monitor 210. The planes or angles of orientation of the planes can be determined by input from the operator received over MCM-operator-interface 610 and/or a plane can be defaulted to be one of the transverse planes (i.e., planes perpendicular to the optical axis of objective lens 110) for a direction examined by the neurosurgeon. For example an image of a particular plane generated from 3D OCT scan data of brain 1000 provides a cross section of brain 1000 at a particular depth along a particular direction. Due to different backscattering properties of various structures in brain 1000, the images generated from the OCT scan data, for example, a cross section provided by the OCT raster scan, help a neurosurgeon locate nerves and blood vessels concealed by brain tissue or locate a brain tumor. Further, the neurosurgeon can identify various structures in the images provided by the OCT scan data by outlining them using MCM-operator-interface 610 in the same manner described above with respect to CT/NMR diagnostic image data, i.e., causing MCM-computer-system 500 to generate a boundary from operator input of several points along the boundary using MCM-operator-interface 610. Still further, for structures which have sufficiently different contrast from surrounding tissue, MCM-computer-system 500 can create a boundary by using analytic techniques which are well known in the art for detecting the boundary between areas of different intensity. Yet still further, the neurosurgeon can cause MCM 600 to move to various positions along a displayed boundary of the structure in response to input from MCM-operator-interface 610 and to move a surgical instrument such as a laser apparatus and/or an electrocautery apparatus to bear at the focus of neurosurgical microscope 100 for the purpose of cutting tissue along the boundary.

In a second method of utilizing the OCT scan data in accordance with the present invention, images of cross sections of brain 1000 provided by analysis of the OCT scan data are correlated with stored diagnostic image data such as CT/NMR diagnostic image data to improve the resolution of the diagnostic image data. As is well known, during a surgical procedure, as MCM 600 continuously rotates and translates neurosurgical microscope 100, MCM-computer-system 500 continuously rotates and translates the three dimensional ("3D") data set of stored CT/NMR diagnostic image data according to the rotational and translational coordinates of MCM 600. During this time, as neurosurgical microscope 100 is rotated and translated, in accordance with the present invention, OCT scan data are continuously acquired. As was described above, the CT/NMR diagnostic image data correspond to the respective coordinates of tissue in brain 1000 only with an accuracy on the order of millimeters. For that reason, there is a rotational and translational offset, also on the order of millimeters, between the OCT scan data and the CT/NMR diagnostic image data. In accordance with the present invention, during a correlation procedure which will be described in detail below, the CT/NMR diagnostic image data are further rotated and translated to maximize a correlation function of the OCT scan data and the CT/NMR diagnostic image data. At the orientation and position which produces a maximum correlation, the true position of brain 1000 is known to MCM-computer-system 500. MCM-computer-system 500 then corrects the CT/NMR diagnostic image data and displays the corrected diagnostic image data, for example, on video monitor 210.

The correlation between the OCT scan data and the diagnostic image data is performed as follows. A feature in brain 1000 is located, for example, by pattern recognition. The pattern recognition algorithm used may be any standard pattern recognition algorithm and, as will be readily understood by those of ordinary skill in the art, the particular pattern recognition algorithm used is not critical to the operation of the present invention. Alternatively, a feature in brain 1000 and/or a particular location to use as a feature may be indicated by the neurosurgeon as he/she views the diagnostic image data displayed on video monitor 210. The neurosurgeon makes the indication, for example, by using MCM-operator-interface 610. Next, coordinates of the feature in the OCT scan data are determined in a manner that will be described in detail below and coordinates of the feature in the diagnostic image data are determined in a manner that will be described in detail below. Next, a correlation is performed between the two sets data for the coordinates in a manner that will be described in detail below. Finally, the result of the correlation is used to improve the resolution of the diagnostic image data and to change the position of the autofocus of neurosurgical microscope 100 in a manner that will be described in detail below. Although the depth of penetration of OCT radiation into brain tissue is only one to two millimeters because of the high scattering strength of brain tissue, by linking the OCT scan data with the diagnostic image data in accordance with the present invention, the resolution of the diagnostic image data is improved. Finally, MCM-computer-system 500 combines the OCT scan data (the OCT scan data can identify and/or properly locate blood vessels and nerves) with the diagnostic image data to provide a single display which indicates corrected (or newly discovered) locations of the blood cells and nerves. As one can readily appreciate, the neurosurgeon can use the single display, for example, by means of light pen input, to cause MCM 600 to move to locations which avoid the blood vessels and/or nerves.

In particular, the above-described correlation procedure is carried out as follows.

Step 1: Using diagnostic image data, during the planning stage of a neurosurgical procedure, the neurosurgeon identifies critical feature(s) in a patient's brain like nerves and blood vessels near a planned channel by identifying a region containing the critical feature(s) in, for example, predetermined sections of the diagnostic image data with a light pen or other pointer device (a predetermined section of the diagnostic image data is a set of the diagnostic image data which produces an image in a plane which has a predetermined orientation). Typically, a region comprises for example, a circular area of predetermined size, which area is larger than the critical feature(s). The critical feature(s) are delimited in accordance with the present invention by boundary lines in of the predetermined sections of the diagnostic image data. For example, in one embodiment of the present invention, such boundary lines enclose an area of the section of the diagnostic image data comprised of pixels whose gray values differ from those of pixels in a surrounding area of the section of the diagnostic image data. In such an embodiment, a boundary line may be defined using a threshold algorithm as follows. In a region within, for example, a circular area having a predetermined radius, the circle being centered at a point indicated by the neurosurgeon using the light pen, the gray values of all pixels within this region are sorted into a histogram showing the number of pixels with a certain gray value. As one of ordinary skill in the art will readily appreciate, in accordance with the present invention, the size of the predetermined radius will vary, depending on the typical size of the critical feature(s). Further, the size of the radius may be varied by the neurosurgeon by providing input using MCM-operator-interface 610. Still further, the area used may be a square having a side of predetermined size or various other shapes may be used. In accordance with this embodiment of the present invention, there are two classes of gray values. Pixels within the critical feature(s) cluster in the histogram at a different gray value (gray value 1) than pixels outside of the critical feature(s) (gray value 2). In accordance with this embodiment, pixels with a gray value larger, for example, than (gray value 1-gray value 2)/2 are set to 1. The other pixels are set to 0. These binary data and the coordinates of the pixels are stored as a separate data set called binary diagnostic image data in the following steps.

Step 2: Using OCT scan data, during the neurosurgical procedure, the neurosurgeon identifies the critical feature(s) in corresponding sections of the OCT scan image by identifying a region containing the critical feature(s) in the OCT scan image with a light pen or other pointer device. Typically, the region comprises for example, a circular area of predetermined size, which area is larger than the critical feature(s). Further, the neurosurgeon associates the critical feature(s) identified in the OCT scan image with the critical feature(s) identified in the diagnostic image data using, for example, MCMoperator-interface 610. The pixels of OCT scan data in the OCT section in the critical feature(s) differ from the pixels of OCT scan data in the OCT section in an area surrounding the critical feature (s) in respect to their gray value because of the significantly different scattering and absorption properties of the critical feature(s). Therefore, in accordance with the present invention, pixels in the critical feature(s) can be identified using the same classification procedure described above in step 1 for identifying pixels in the critical feature(s) in diagnostic image data. The result is a binary OCT scan data set of binary data and the coordinates of the pixels wherein pixel values equal 1 for pixels within critical feature(s) and pixel values equal 0 for pixels outside of critical feature(s). It should be clear that the association of critical feature(s) in the two sets of data may be done before creation of the binary data sets or afterwards using side by side or overlayed images of the binary pixel values.

Step 3: As was described above, the coordinates of pixels in the OCT scan data are known by MCM-computer-system 500 because OCT transverse scanner 420 and the optics in OCT generator and analyzer 400 are rigidly attached to neurosurgical microscope 100. As was further described above, and as is well known, the microscope/MCM coordinates are transformable into the coordinate system of the diagnostic image data. In accordance with the present invention, the coordinates of the OCT scan data corresponding to the binary OCT scan data set are transformed to the diagnostic image coordinate system. As a result, MCM-computer-system 500 has binary diagnostic data sets in the diagnostic image coordinate system for the sections and binary OCT scan data sets in the diagnostic image coordinate system for the corresponding sections. However, the diagnostic and OCT scan data sets differ in position because of the above-mentioned inaccuracy, on the order of a millimeter, between diagnostic image coordinates and MCM coordinates. In accordance with the present invention, binary OCT data sets are correlated with binary diagnostic image data sets, in corresponding sections, in accordance with step 4.

Step 4: M is a binary diagnostic image data set matrix for a section and N is a transformed binary OCT scan data set matrix for the corresponding section (i.e., transformed to the diagnostic coordinate system). The rows and columns of each matrix correspond to the pixel values in each of the data sets for pixels covering the area of a critical feature. For example, the rows correspond to the x-direction and the columns correspond to the y-direction. For the sake of simplicity, let us assume that both matrices are n*n matrices. The correlation function is then determined by the following procedure.

1) I=0,J=0
2) A(I, J)=Σover (i=1→n,j=1→n) of {M(i+I,j+J)* N(i,j)}
3) I=I+1
4) IFI<n GO TO 2
5) J=J+1
6) IFJ<n GO TO 2

The resulting correlation function A(I,J) has a maximum value at (row, column) given by ($I_{max}$, $J_{max}$), which maximum value corresponds to the best fit between the binary OCT scan data set and the binary diagnostic image data set. The distance s between diagnostic image data pixels is known. As a result, the offset between the OCT scan data and the diagnostic image data is $s*I_{max}$ in the x-direction and $s*J_{max}$ in the y-direction. The displacement values are then used to shift the diagnostic image data to its true position.

Step 5: The above-described procedure enables MCM-computer system 500 to fit the diagnostic image data coordinates to the true patient coordinates in the one section. Then, in accordance with the present invention, another section having a different orientation is needed to fit the diagnostic image data coordinates to the true patient coordinates in all three dimensions. For example, in accordance with a preferred embodiment of the present invention, a second section is a plane which is oriented in an orthogonal direction to the first section. For example, if the plane of the first section is designated as the x-y plane, the plane of the second, orthogonal section is designated as the y-z plane. As was explained, the data corresponding to the various planes is obtained from the 3D OCT scan data. Then one repeats step 4 to obtain another correlation function $A'(J, K)$ with a maximum value at (row, column) given by $(J_{max}, K_{max})$. As a result, the offset between the OCT scan data and the diagnostic image data is $s*J_{max}$ in the y-direction (already determined with the first section) and $s*K_{max}$ in the z-direction.

In a third method of utilizing the OCT scan data in accordance with the present invention, OCT generator and analyzer 400 is fabricated in accordance with the embodiment shown in FIG. 4. In accordance with the present invention, such an embodiment of OCT generator and analyzer 400 is used to fabricate the apparatus shown in FIG. 1 for differentiating between a brain tumor and normal brain tissue. As shown in FIG. 1 of an article entitled "Noninvasive Methods for Estimating In Vivo Oxygenation" by David A. Benaron, William E. Benitz, Ronald L. Ariagno, and David K. Stevenson, *Clinical Pediatrics*, May 1992, pp. 258–273, absorption of oxyhemoglobin ($HbO_2$) and hemoglobin (Hb) is different and, in particular, such absorption is different below and above 800 nm. Specifically, as shown in the article, at about 800 nm, the absorption of oxyhemoglobin is equal to the absorption of hemoglobin, this being known as the isobestic point.

In accordance with the present invention, MCM-computer-system 500 measures light flux backscattered from tissue at three wavelengths to distinguish between tissue structures having different oxygen pressures. The inventive method and apparatus is understood in accordance with the following explanation.

OCT beam 430 described above hits the surface tissue of brain 1000 with an intensity $I_{in}(0)$. OCT beam 430 beam penetrates the tissue of brain 1000 and is attenuated. The attenuation is due to scattering and absorption and can be described by the following differential equation of intensity of the radiation at position z within brain 1000. Distance z is the distance between the surface of brain 1000 ($z=0$) and axial position z.

$$dI(z)/dz = -a(z)I(z) \quad (1)$$

where $a(z)$ is a position dependent attenuation coefficient comprised of a scattering factor $S(z)$ and an absorption factor $A(z)$. Differential eqn. (1) then becomes:

$$dI(z)/dz = -S(z)A(z)I(z) \quad (2)$$

The solution of differential eqn. (2) is given by:

$$I(z) = I_{in}(0)\exp[-\int_0^z S(z')A(z')dz'] \quad (3)$$

At each axial position z, radiation is scattered back in the direction of the incoming beam. The scattering strength depends on the scattering factor $S(z)$, but only a fraction a is gathered by fiber 250 OCT generator and analyzer 400. The intensity of the backscattered radiation also depends on the intensity at position z. The backscattered radiation is further attenuated by tissue lying between axial position z and surface of brain 1000 at $z=0$. The resultant intensity of the backscattered radiation at the surface of brain 1000, i.e., at axial position $z=0$ is given by:

$$I_{back}(0, z) = I_{in}(0)\sigma S(z)\exp[-2\int_0^z S(z')A(z')dz'] \quad (4)$$

The scattering factor $S(z)$ is typically not wavelength dependent over a broad wavelength range. However, as shown by the above-identified article of Benaron et al., the absorption coefficient $A(z)$ is significantly wavelength dependent. In accordance with the present invention, three light sources with wavelengths $\lambda_1$, $\lambda_2$ and $\lambda_3$, respectively, are used (see the description above of the embodiment shown in FIG. 4). The intensities at the surface of brain 1000 ($z=0$) of the radiation backscattered from axial position z are given by:

$$I_{back}(\lambda_i, 0,z) = I_{in}(\lambda_i)\sigma SS(z)\exp[-2\int_0^z S(z')A(\lambda_i, z')dz'] \quad (5)$$

where $i=1, 2, 3$. For the sake of simplicity and ease of understanding the present invention, assume that $I_{in}(\lambda_i)$ is the same for all three wavelengths. With straightforward transformations, one obtains:

$$\{d/dz\}\ln[I_{back}(\lambda_1, 0, z)/I_{back}(\lambda_2, 0,z)] = -2S(z)\{A(\lambda_1,z) - A(\lambda_2,z)\} \quad (6)$$

$$\{d/dz\}\ln[I_{back}(\lambda_3, 0, z)/I_{back}(\lambda_2, 0,z)] = -2S(z)\{A(\lambda_3,z) - A(\lambda_2,z)\} \quad (7)$$

From eqns. (6) and (7), one obtains:

$$|A(\lambda_1, z) - A(\lambda_2, z)|/|A(\lambda_3, z) - A(\lambda_2, z)| = \quad (8)$$

$$\frac{\{d/dz\}\ln[I_{back}(\lambda_1, 0, z)/I_{back}(\lambda_2, 0, z)]}{\{d/dz\}\ln[I_{back}(\lambda_3, 0, z)/I_{back}(\lambda_2, 0, z)]}$$

Absorption coefficient $A(\lambda_i, z)$ depends on the concentration, $C_{ox}(z)$, and the absorption coefficient, $a_{ox}(\lambda_i)$ of oxygenated hemoglobin and on the concentration, $C_{non}(z)$, and the absorption coefficient, $a_{non}(\lambda_i)$, of non-oxygenated hemoglobin as follows:

$$A(\lambda_i,z) = C_{ox}(z)a_{ox}(\lambda_i) + C_{non}(z)a_{non}(\lambda_i) \quad (9)$$

where $i=1, 2, 3$. Using eqn. (9), one obtains the following equation for oxygen saturation $R(z)$:

$$R(z) = C_{ox}(z)/[C_{ox}(z) + C_{non}(z)] = 1/\{1 + (d*f - b)/(a - c*f)\} \quad (10)$$

where:

$a = a_{ox}(\lambda_1) - a_{ox}(\lambda_2)$
$b = a_{non}(\lambda_1) - a_{non}(\lambda_2)$
$c = a_{ox}(\lambda_3) - a_{ox}(\lambda_2)$
$d = a_{non}(\lambda_3) - a_{non}(\lambda_2)$
$f = \{d/dz\}\ln[I_{back}(\lambda_1,0,z)/I_{back}(\lambda_2,0,z)]/\{d/dz\}\ln[I_{back}(\lambda_3, 0,z)/I_{back}(\lambda_2,0,z)]$ Using the above-described equations, one calculates the oxygen saturation $R(z)$ at position z within the brain tissue when the backscattered intensities $I_{back}(\lambda_i, 0,z)$ are measured spatially resolved in accordance with the OCT method described above. The relative absorption coefficients $a_{ox}(\lambda_i)$ and $a_{non}(\lambda_i)$ may be obtained experimentally or they may be taken from the above-identified article by Benaron et al.

In accordance with the present invention, OCT scan data are acquired using OCT radiation generated at three different wavelengths. Image signal intensities are determined by determining the respective signal strengths at each pixel of the OCT scan data. Using this information, MCM-computersystem 500 determines the oxygen saturation for each of the pixels in the OCT scan data in accordance with the method described in detail above with respect to eqns. (1)-(10). The OCT scan data are used to provide images in various planes showing oxygen saturation. Advantageously, in accordance with the present invention, such images of oxygen saturation are provided with a resolution determined by OCT generator and analyzer 400 to an accuracy on the order of ten to twenty micrometers. MCM-computer-system 500 transmits the images to video monitor 210 for display on at least a portion of the screen of video monitor 210 to enable a neurosurgeon to locate a brain tumor. Using oxygen saturation data over a 3D volume, a neurosurgeon by input (using MCM-operator-interface 610) or MCM-computer-system 500 (using feature recognition techniques described above) or a combination of both can utilize the oxygen saturation data to identify and/or locate a brain tumor. For example, after an image of oxygen saturation is displayed, the neurosurgeon may indicate tumor tissue outline by input such as by light pen. In a further embodiment, MCM-computer-system 500 may identify tumor tissue by using a threshold value of oxygen saturation to provide a boundary.

In addition, MCM-computer-system 500 combines the OCT data images with the diagnostic image data to provide a single display which the neurosurgeon may use to identify a brain tumor. This is done as follows. The values of the pixels of the three dimensional OCT data set which has been identified as tumor tissue as described above are set to 1 and the values of all other pixels are set to 0. The new pixel values and the coordinates of the pixels are stored in a binary OCT scan data set. Next, the procedure described above for correlating the OCT scan data and the diagnostic image data is applied to the binary OCT scan data set. The transformed binary OCT scan data coordinates are then isometric with the three dimensional diagnostic image data field and the MCM coordinate system. In one embodiment of the present invention, for display purposes, the binary OCT scan data values are added pointwise, i.e., pixel by pixel, to the diagnostic image data. Based on the position/orientation of the MCM cross section, the diagnostic image data set corresponding to the focal plane of neurosurgical microscope 100 is displayed on video monitor 210 with the corresponding cross section of the OCT scan data set as an overlay. For better distinction between the images, the OCT scan data overlay can be realized as a false color pattern.

Those skilled in the art will recognize that the foregoing description has been presented for the sake of illustration and description only. As such, it is not intended to be exhaustive or to limit the invention to the precise form disclosed. For example, although the present invention has been described in terms of a neurosurgical procedure and a neurosurgical microscope, the present invention is not so limited. In fact, the present invention relates to surgical procedures and surgical microscopes in general and to surgical procedures carried out on any portion of a body, whether human or animal.

What is claimed is:

1. A surgical apparatus for use in performing a surgical procedure on an object which comprises:

a surgical microscope;

a multi-coordinate manipulator ("MCM") system which: (a) translates the surgical microscope and orients an optic axis of the surgical microscope, (b) stores diagnostic image data, and (c) autofocuses the surgical microscope; and an optical coherence tomography ("OCT") apparatus which includes: (a) a scanner which scans the object with optical output from the OCT apparatus in response to input from the MCM system, (b) a receiver which produces OCT scan data in response to reflections of the optical output from the object, and (c) a transmitter which transmits the OCT scan data to the MCM system for analysis.

2. The surgical apparatus of claim 1 wherein the MCM system further comprises:

an analyzer which analyzes the OCT scan data to obtain OCT scan data in planes and which combines the OCT scan data in the planes to provide OCT scan data in a three dimensional volume.

3. The surgical apparatus of claim 2 wherein the MCM system further comprises a display which displays OCT images of the OCT scan data in planes having various orientations through the three dimensional volume.

4. The surgical apparatus of claim 3 wherein the display further displays diagnostic images of the diagnostic image data in planes having the various orientations through the three dimensional volume.

5. The surgical apparatus of claim 4 wherein the display further displays the OCT images and the diagnostic images at the same time.

6. The surgical apparatus of claim 5 wherein the display further displays overlays of the OCT images and the diagnostic images.

7. The surgical apparatus of claim 4 wherein the MCM system further comprises an identifier which identifies features in the diagnostic image data and in the OCT scan data in corresponding planes.

8. The surgical apparatus of claim 7 wherein the identifier further comprises an associater which associates features in the diagnostic image data with features in the OCT scan data.

9. The surgical apparatus of claim 8 wherein the MCM system comprises a correlator which correlates associated features in the diagnostic image data and the OCT scan data and a transformer which transforms the diagnostic image data in response to output from the correlator.

10. The surgical apparatus of claim 9 wherein the display further displays the transformed diagnostic image data in planes having various orientations through the three dimensional volume.

11. The surgical apparatus of claim 10 wherein the display further displays combined images of the OCT scan data and the transformed diagnostic image data in the planes.

12. The surgical apparatus of claim 1 wherein the optical output from the OCT apparatus comprises first radiation having substantially a first wavelength from a first source, second radiation having substantially a second wavelength from a second source and third radiation having substantially a third wavelength from a third source.

13. The surgical apparatus of claim 1 wherein the optical output from the OCT apparatus comprises first radiation having substantially a first wavelength, second radiation having substantially a second wavelength and third radiation having substantially a third wavelength and wherein the OCT scan data comprises first OCT scan data produced by the first radiation, second OCT scan data produced by the second radiation, and third OCT scan data produced by the third radiation.

14. The surgical apparatus of claim 13 wherein the MCM system further comprises:

a comparison analyzer which analyzes the first, second and the third OCT scan data to identify one type of tissue from another type of tissue.

15. The surgical apparatus of claim 14 wherein the comparison analyzer comprises a measurer which measures oxygen saturation data for a three dimensional volume from which the OCT scan data is produced by the first radiation, the second radiation, and the third radiation.

16. The surgical apparatus of claim 14 wherein the comparison analyzer comprises a property measurer which measures a property of tissue contained in a three dimensional volume from which the OCT scan data is produced by the first radiation, the second radiation, and the third radiation.

17. The surgical apparatus of claim 16 wherein the MCM system further comprises an identifier responsive to output from the property measurer which identifies a first type of tissue from at least another type of tissue by grouping OCT scan data having predetermined values of the property.

18. The surgical apparatus of claim 16 wherein the MCM system further comprises a display which displays OCT images of the OCT scan data showing the property in planes having various orientations through the three dimensional volume.

19. The surgical apparatus of claim 18 wherein the MCM system further comprises an MCM operator interface which receives user input and wherein the display comprises an identifier which identifies one type of tissue from another type of tissue in response to the user input.

20. The surgical apparatus of claim 17 wherein the MCM system further comprises a correlator which correlates the first type of tissue identified in the OCT scan data with diagnostic image data and a transformer which transforms the diagnostic image data in response to output from the correlator.

21. The surgical apparatus of claim 20 wherein the MCM system further comprises a display which displays diagnostic image data in planes having various orientations throughout the three dimensional volume and which displays a representation of the first type of tissue identified in the OCT scan data.

22. The surgical apparatus of claim 21 wherein the display further displays the representation of the first type of tissue identified in the OCT scan data as an overlay.

23. The surgical apparatus of claim 22 wherein the overlay is a false color pattern.

24. A method of performing a surgical procedure on an object which comprises the steps of:

translating a surgical microscope, orienting an optic axis of the surgical microscope and autofocusing the surgical microscope;

scanning the object with optical output from an optical coherence tomography apparatus and producing OCT scan data in response to reflections of the optical output from the object; and analyzing the OCT scan data to transform diagnostic image data.

25. The method of claim 24 which further comprises the steps of:

displaying OCT images of the OCT scan data in planes having various orientations throughout a three dimensional volume from which the reflections are obtained.

26. The method of claim 24 wherein the optical output comprises first radiation having substantially a first wavelength, second radiation having substantially a second wavelength and third radiation having substantially a third wavelength; wherein the OCT scan data comprises first OCT scan data produced by the first radiation, second OCT scan data produced by the second radiation, and third OCT scan data produced by the third radiation; and analyzing the first, second and third OCT scan data to measure a property of tissue contained in a three dimensional volume from which the OCT scan data is produced by the first radiation, the second radiation, and the third radiation.

27. The surgical apparatus of claim 7 wherein the MCM system further comprises an MCM operator interface which receives user input and wherein the identifier operates in response to the user input.

28. The surgical apparatus of claim 8 wherein the MCM system further comprises an MCM operator interface which receives user input and wherein the associater operates in response to the user input.

29. The surgical apparatus of claim 9 wherein the MCM autofocuses the surgical microscope in response to the transformed diagnostic image data.

30. The surgical apparatus of claim 11 wherein the combined images are presented in a single display.

31. The surgical apparatus of claim 11 wherein the identifier further identifies sensitive features.

32. The surgical apparatus of claim 31 wherein the MCM system further comprises an MCM operator interface which receives user input and wherein the identifier identifies the sensitive features in response to the user input.

33. The surgical apparatus of claim 32 wherein the MCM system further moves surgical tools to avoid the identified sensitive features.

34. The surgical apparatus of claim 18 wherein the MCM system further comprises an MCM operator interface which receives user input and an identifier which identifies one type of tissue from another type of tissue in response to output from the property measurer and to the user input.

35. The surgical apparatus of claim 19 wherein the MCM system further comprises a correlator which correlates the first type of tissue identified in the OCT scan data with diagnostic image data and a transformer which transforms the diagnostic image data in response to output from the correlator.

36. The surgical apparatus of claim 34 wherein the MCM system further comprises a correlator which correlates the first type of tissue identified in the OCT scan data with diagnostic image data and a transformer which transforms the diagnostic image data in response to output from the correlator.

* * * * *